(12) United States Patent
Savion et al.

(10) Patent No.: US 7,723,287 B1
(45) Date of Patent: May 25, 2010

(54) TREATMENT OF THE EYE WITH A PHARMACEUTICAL COMPOSITION

(75) Inventors: Naphtali Savion, Givat Shmuel (IL); Arieh Solomon, Tel Aviv (IL)

(73) Assignee: Ramot At Tel-Aviv University Ltd., Tel Aviv (IL)

( * ) Notice: Subject to any disclaimer, the term of this patent is extended or adjusted under 35 U.S.C. 154(b) by 0 days.

(21) Appl. No.: 09/341,048

(22) PCT Filed: Jan. 13, 1998

(86) PCT No.: PCT/IL98/00012

§ 371 (c)(1), (2), (4) Date: Aug. 9, 1999

(87) PCT Pub. No.: WO98/30233

PCT Pub. Date: Jul. 16, 1998

(30) Foreign Application Priority Data

Jan. 14, 1997 (IL) .................................... 120005

(51) Int. Cl.
*A61K 38/00* (2006.01)
(52) U.S. Cl. .......................... 514/2; 514/134; 514/912
(58) Field of Classification Search .................... 514/2, 514/134, 912
See application file for complete search history.

(56) References Cited

U.S. PATENT DOCUMENTS 5,023,090 A * 6/1991 Levin .......................... 424/520
5,389,373 A * 2/1995 Davis et al. .................. 424/400

FOREIGN PATENT DOCUMENTS

| EP | 0 312 814 A | 4/1989 |
| EP | 0 733 918 A2 | 3/1996 |
| WO | WO 91/12808 | 9/1991 |
| WO | WO 94/04178 | 3/1994 |
| WO | WO 95/14488 | 6/1995 |

OTHER PUBLICATIONS

Levine et al., In vivo protection against endotoxin by plasma high density lipoprotein, Proc. Natl. Acad. Sci., vol. 90, pp. 12040-12044, XP-002062711.
G. Rieger, Lipid-Containing Eye Drops: A Step Closer to Natural Tears, Opthalmologica, vol. 201, 1990, pp. 201-212, XP-002062710.
Bundesverband Der Pharmazeutischen Industrie E.V.: Rote Liste 1995:, 1995, ECV. Editio Cantor. Aulendort/Wurtt, XP-002062712.

Gordon et al., Topical Fibronectin Ophthalmic Solution in the Treatment of Persistent Defects of the Corneal Epithelium, Am. J. Opthalmol., vol. 119, No. 3, pp. 281-289, 1995.
McGuire et al., Lovastatin Inhibits Platelet-derived Growth Factor (PDGF) Stimulation of Phosphatidylinositol 3-Kinase Activity as well as Association of p85 Subunit to Tyrosine-phosphorylated PDGF Receptor (Communication), J. Biological Chemistry, vol. 268, No. 30, pp. 22227-22230, 1993.
Glomset, The Plasma lecithin: cholesterol acyltransferase reaction, J. Lipid Research, vol. 9, pp. 155-167, 1968.
Gospodarowicz et al., Stimulation of the Proliferation of the Madin-Darby Canine Kidney (MDCK) Epithelial Cell Line by High-Density Lipoproteins and Their Induction of 3-Hydroxy-3-Methylglutaryl Coenzyme A Reductase Activity, J. Cellular Physiology, vol. 117, pp. 76-90, 1983.
Kristin L. Gillotte et al., *Apolipoprotein A-I Structural Modification and the Functionality of Reconstituted High Density Lipoprotein Particles in Cellular Cholesterol Efflux*, 271 J. Bio. Chem. 23792 (1996).
Martin K. Bijsterbosch et al., *Synthesis of Dioleoyl Derivative of Iododeoxyuridine and Its Incorporation into Reconstituted High Density Lipoprotein Particles*, 33 Biochem. 14073 (1994).
Kerry-Anny Rye et al., *The Infleucne of Sphingomyelin on the Structure and Function of Reconstituted High Density Lipoproteins*, 271 J. Bio. Chem. 4243 (1996).
Martin K. Bijsterbosch et al., *Specific Targeting of Lipophilic Prodrug of Iododeoxyuridine to Parenchymal Liver Cells Using Lactosylated Reconstituted High Density Lipoprotein Particles*, 52 Biochem. Pharmacology 113 (1996).
Delmas J. Bolin & Ana Jonas, *Sphingomyelin Inhibits the Lecithin-Cholesterol Acyltransferase Reaction with Reconstituted High Density Lipoproteins by Decreasing Enzyme Binding*, 271 J. Bio. Chem. 19152 (1996).
Masakazu Sakai et al., *Reconstituted high density lipoprotein reduces the capacity of oxidatively modified low density lipoprotein to accumulate cholesteryl esters in mouse peritoneal macrophages*, 119 Atherosclerosis 191 (1996).
Thomas S. Parket et al., *Reconstituted High-Density Lipoprotein Neutralizes Gram-Negative Bacterial Lipopolysaccharides in Human Whole Blood*, 63 Infection & Immunity 253 (1995).
Daniel L. Sparks et al., *The Conformation of Apolipoprotein A-I in Discoidal and Spherical Recombinant High Density Lipoprotein Particles*, 267 J. Bio. Chem. 25830 (1992).
Mary C. Ritter & Angelo M. Scanue, *Role of Apolipoprotein A-I in the Structure of Human Serum High Density Lipoproteins*, 252 J. Bio. Chem. 1208 (1977).

* cited by examiner

*Primary Examiner*—Zohreh A Fay
(74) *Attorney, Agent, or Firm*—The Nath Law Group; Susanne M. Hopkins; Ari G. Zytcer (57) ABSTRACT

A pharmaceutical composition for the treatment of disorders of the anterior segment of the eye or for the preservation of isolated cornea. The composition comprises, as an active ingredient, an agent capable of causing a net efflux of cholesterol from cells.

61 Claims, 9 Drawing Sheets

TREATMENT OF THE EYE WITH A PHARMACEUTICAL COMPOSITION

RELATED APPLICATION

This is a U.S. National Phase Application of PCT Application Ser. No. PCT/IL98/00012; filed 13 Jan. 1998, which in turn is based on Israeli Application No. 120005, filed 14 Jan. 1997, the priority of which is claimed herein.

FIELD OF THE INVENTION

The present invention concerns pharmaceutical compositions for the treatment of the eyes and more specifically for the treatment of disorders of the anterior segment of the eye.

BACKGROUND OF THE INVENTION

The protective structures of the anterior surface of the eye include the eyelids, conjunctiva, and the cornea. The posterior surfaces of the lids are covered with a mucous membrane and the palpebral conjunctiva which reflects onto the eye to become the bulbar conjunctiva. The bulbar conjunctival epithelium is continuous with the corneal epithelium which accounts for about 10% of the anterior surface of the eye and is where most of the stationary refraction occurs.

The corneal epithelium is 4-5 cells thick and the superficial cells contain many microvilli. These aid in maintaining the moisture of the epithelial surface by promoting the adhesion of the tear film to the surface. This film lubricates the anterior surface of the eye to decrease the frictional forces arising from the persistent blinking movements of the eyelids, foreign particles on the surface of the eye, and the rotational movements of the eyeball. The tear film also transfers oxygen from ambient air to the cornea.

The anterior surface of the eye is vulnerable to damages inflicted by various causes including mechanical abrasion of the cornea; contact lens wearing; spontaneous peeling of the epithelium; damaged epithelium and stroma following photo-refractive keratectomy; chemical burns; over exposure to ultraviolet light including sunlight; systemic diseases such as Sjogren syndrome, Steven-Johnson syndrome, Cicatricial pemphigoid syndrome; chronic edema of cornea with recurrent erosion of epithelium; impaired tear film formation, and conditions following damage of epithelia due to radial keratotomy.

Aging often causes disorders resulting from slow regeneration of the epithelium. The impaired regeneration and abnormality of the cells causes thinning of the epithelial layer and its impaired adherence to the basal lamina thus decreasing the ability of the cornea to retain the tear film leading to further epithelial damage.

Following injury to the corneal epithelium, nearby cells retract slightly, round up and begin an ameboid migration from the basal layer across the exposed basement membrane to cover the defect with a new monolayer of cells. These cells then take on the characteristics of a new basal layer and undergo mitosis to gradually fill in the defect with the full complement of four to five layers of cells. Present treatment for corneal wounds involves applying eye drops to the surface in order to protect the delicate healing process from erosion due to blinking and the other sources of friction. There are no currently used medicaments that promote the healing process itself. Attempts to administer fibronectin in order to promote healing of persistent defects of the corneal epithelium failed (Fukuda et al., *Am J. Ophthalmol.*, 119(3):281-287, (1995)).

It would have been highly desirable to provide an ophthalmic composition capable of protecting the corneal epithelium and enhancing its healing and regeneration.

The rate of cell proliferation in many cell types has been correlated with the rate of cholesterol synthesis, and more specifically with the biosynthesis of various intermediates in the cholesterol biosynthesis pathway and their by-products such as farnesylated proteins and others. Thus, inhibition of an early enzyme in the biosynthesis of cholesterol inhibits cell growth in cultured fibroblasts (McGuire et al., *J. Biol. Chem.*, 268:22227-22230, (1993)). Factors which cause cholesterol efflux from cells (e.g. high density lipoproteins, HDL) alleviate the negative feedback inhibition of cholesterol synthesis and enhance growth of MDCK cells in vitro (Gospodarowicz et al., *J. Cell. Physiol.*, 117:76-90, (1983)).

The cornea is an avascular organ obtaining nutrition from the vasculature of the limbus by diffusion. At the outer surface of the cornea, the epithelium is essentially isolated from the plasma's large complexes such as HDL which hardly diffuse through the cornea. Thus, HDL which performs the "reverse cholesterol transport" from peripheral organs to the liver (Glomset, J. A., *J. Lipid Res.*, 9:155-167, 1968) is unable to perform this task in the corneal epithelium.

SUMMARY OF THE INVENTION

The present invention is based on the surprising finding that high density lipoprotein (HDL), or a combination of its non-cholesterol lipid constituents (phospholipids, and other lipids such as triglycerides and glycerol), which are capable of forming reconstituted HDL, promotes normal healing and regeneration of damaged eye epithelium.

Both HDL and said lipid constituents were able to initiate the process of healing, to increase its rate, and to promote reversion of the damaged epithelium of the eye to the normal state, i.e. where the damaged area is covered again by layers of epithelial cells.

Thus, the present invention concerns a pharmaceutical composition for the treatment of disorders of the anterior segment of the eye comprising, as an active ingredient, at least one agent capable of causing a net efflux of cholesterol from cells, together with an opthalgestically acceptable carrier.

The term "treatment" refers to curing of the disorder of the eye, to alleviation of some of the undesired symptoms of various eye disorders, and/or to prevention of various eye disorders before they are manifested.

The term "anterior segment of the eye" refers to the corneal and conjunctival epithelium and includes the epithelial cells, as well as the glands present in the epithelium.

The term "disorders of the anterior segment of the eye" refers to disorders which cause physical damage to the corneal or conjunctival epithelium, to disorders which decrease the rate of regeneration of cells making up this epithelium, or to disorders causing diminished secretions from glands present in the conjunctival epithelium, or to a combination of some of these disorders.

Typical disorders of the anterior segment of the eye caused by physical or chemical damage are: mechanical abrasion of the cornea, corneal epithelial defects created by wearing contact lenses, corneal epithelial defects created by spontaneous peeling of the epithelium, corneal damage following photoreactive keratectomy, injuries caused by chemical substances, damage caused by exposure to ultraviolet light, systemic diseases creating damage to the corneal epithelium and conjunctiva, for example, Sjorgren-Syndrome, Steven-Johnson Syndrome, Cicatricial Pemphigoid Syndrome, chronic edema of the cornea with recurrent erosion of epithelium and the like.

Typical disorders of the anterior segment of the eye caused by a decrease in the rate of generation of cells include deterioration of the eye due to old age or an anti-proliferative treatment.

The pharmaceutical composition of the present invention may be administered to persons suffering from disorders which cause damage to the corneal or conjunctival epithelia, or in conjunction with treatments which are known to cause such damage, for example, laser or radial keratectomy or administration of various systemic or topical medications.

The active agents of the invention are those capable of causing a net efflux of cholesterol from cells. Locating candidate agents capable of generating a net cholesterol efflux, may be carried out, for example, by determining the net efflux of labeled cholesterol from cells according to the method described in Naphtali Savion and Shlomo Kotev-Emeth, *Eur. J. Biochem.*, 183:363-370 (1989). Briefly, confluent endothelial or smooth muscle cultures are allowed to incorporate $^3$H-cholesterol. The candidate to be tested as an effector of cholesterol efflux is then added to the cell culture and the percentage of radioactivity remaining in the cells after 24 hrs. is determined. Candidates which are able to significantly lower the amount of labeled cholesterol in these cells, are those which are capable of serving as active agents in the pharmaceutical compositions of the invention.

Preferably, the present invention concerns a pharmaceutical composition for the treatment of disorders of the anterior segment of the eye comprising as an active agent at least one compound selected from the group consisting of:
i. high density lipoprotein (HDL);
ii. a composition of matter termed "reconstituted HDL" and sphingolipids comprising phospholipids and at least one other lipid component of HDL other than cholesterol and cholesteryl-ester; and
ii. at least one HDL Apolipoprotein.

The term "high density lipoprotein" refers to lipoproteins which may be isolated from humans or other mammalian sources (e.g. bovine plasma), for example, as specified in Denis Gospodarowicz "Methods for Preparation of Media, Supplements, and Substrata for Serum-Free Animal Cell Culture", pp. 69-86, 1984, Alan R. Liss, Inc., New York, N.Y. or other isolation methods based on the density of the HDL.

The term "phospholipids", refers to phospholipids which naturally occur in HDL such as phosphatidylcholine, phosphatidylserine and phosphatidylinositol. An example of "sphingolipids" is sphingomyelin.

The term "and at least one other lipid component of HDL other than cholesterol and cholesteryl-ester" refers to glycerides, glycerol and triglycerides. In accordance with the invention glycerides and triglycerides which are not present naturally in HDL, but have an analogous function to glycerides and triglycerides present in HDL may also be used. The composition of matter comprising the non-cholesterol and the non-cholesteryl-ester lipid components of HDL (generally phospholipids, triglycerides and glycerides) is termed "reconstituted HDL" (Gillote et al., *J. Biol. Chem.*, 271: 23792-23798, 1996). This term refers to a complex comprising phospholipids, triglycerides and glycerides, which differs from natural HDL by the absence of cholesterol, cholesteryl-esters, and apolipoproteins.

Reconstituted HDL particles are prepared by the chelate dispersion/Bio-Bead removal technique (Sparks et al., *J. Biol. Chem.* 267:25830-25838, 1992). Typically, compounds which are used in intravenous nutrition as a source of essential fatty acids, are suitable for serving as the lipid components of HDL. Example being Intralipid™, (Pharmacia AB, Sweden), Lipofundin™ (Braun Melsungen A G, Germany) and others.

The term "HDL apolipoproteins" refers typically to apolipoprotein A-I, A-IV and E-apolipo-proteins or a combination thereof, either isolated from a human or mammalian source (Savion and Gamliel, *Arteriosclerosis*, 8:178-186, 1988). Apolipoprotein-E is purified according to Wernette-Hammond et al., *J. Biol. Chem.*, 264:9094-9101, 1989. The HDL apolipoproteins may also be prepared by various genetic engineering methods described in Breslow, et al., *Proc. Natl. Acad. Sci.*, 79:6861-6865, 1982. For example: Human Apolipoprotein A-I gene can be prepared according to the method of Karathanasis et al., *Proc. Natl. Acad. Sci.*, 80:6147-6151, 1983; Human Apolipoprotein A-IV gene according to Elshourbagy, et al., *J. Biol. Chem.*, 262:7973-7981, 1987; and Human Apolipoprotein E gene according to Das, et al., *J. Biol. Chem.*, 260: 6240-6247, 1985; Paik, et al., *Proc. Natl. Acad. Sci.*, 82:3445-3449, 1985.

The composition of the present invention may further comprise albumin.

Albumin is the most abundant plasma protein and serves as the plasma carrier of free fatty acids. Each albumin molecule has 27 binding sites for fatty acids. Albumin may thus serve as a scavenger for toxic free fatty acids released by damaged anterior chamber tissue included in reconstituted HDL.

The pharmaceutical compositions of the invention may further comprise other ingredients having ophthalgesic affects, especially those which are known to facilitate healing and regeneration of cornea and conjunctiva such as growth factors, for example, keratinocyte growth factor (KGF/FGF7), or epidermal growth factor (EGF) and other growth factors of the EGF family known in the art; various attachment factors such as laminin or fibronectin, and extracellular matrix components such as collagen, heparan sulfate proteoglycans and others.

The pharmaceutical compositions of the invention may also include agents capable of providing ultraviolet light protection, such as oxybenzone 3%, and other such preparations known in the art.

The pharmaceutical compositions of the invention should be administered in the form of eye drops or eye salves together with opthalgestically acceptable carriers. The composition may be in the form of an emulsion, micelles liposomes, etc. The concentration of the active ingredients in the composition should be in the range of 0.1-20%, preferably 0.2-10%, most preferably 0.2-2%.

Some disorders of the eye that are to be treated by the pharmaceutical compositions of the invention include diminished liquid clearance from the eye causing water retention which eventually leads to the rupture of the eye membranes. In such cases, it is preferable that the compositions of the invention be presented in a hyperosmotic formulation which can serve to draw excess liquid from the eye. Such hyperosmotic formulation may be formed, for example, by the addition of NaCl to the composition.

By another aspect, the invention comprises a method for the treatment of disorders of the anterior segment of the eye comprising administering to a subject in need of such treatment at least one agent capable of causing a net efflux of cholesterol from cells.

By another aspect, the invention comprises use of at least one agent capable of causing a net efflux of cholesterol from cells for the preparation of a medicament for the treatment of disorders of the anterior segment of the eye.

By yet another aspect, the present invention concerns a storage preparation for storing and maintaining isolated corneas, for example, in an eye bank. In order to maintain the viability of epithelial cells as well as the exposed endothelium of the eye, it is preferable to add to the storage medium an effective amount of at least one agent capable of causing a net efflux of cholesterol from cells, as explained above.

The invention now will be illustrated with reference to some non-limiting drawings and examples.

DETAILED DESCRIPTION OF THE INVENTION

I. Experimental Procedures

A. Animal Model of Corneal Epithelium and Conjunctival Epithelium Damage

A rabbit model for keratoconjunctivitis (Gilbard et al., *J. Inv. Ophthal. Vis. Sci.*, 2:225-228 (1987)) was used with slight modification. Surgery performed on anesthetized rabbits using a surgical microscope (Inami, Japan) involved excision of the plical fold over the eye, occlusion of the lacrimal duct, and peeling of the palpebral and bulbar conjunctiva. This surgery was done on one eye of 20 rabbits of average age 3 months of both sexes. Surgery and all subsequent treatments were done in accordance with ARVO rules for animal care in research. Tear film osmolarity is elevated by postoperative day 1. Corneal epithelial glycogen levels decline progressively, and conjunctival goblet cell density decreases. These pathologies lead to corneal epithelium damage covering the entire corneal surface by the fifth postoperative day, and it was at this time that treatment of the eyes commenced.

B. HDL Preparation

HDL was prepared from human plasma by differential ultracentrifugation flotation (Havel et al., "Distribution and chemical composition of ultracentrifugally lipoproteins in human serum", *J. Clin. Invest.*, 34:1345-53, (1995)).

C. Evaluation of Rabbit Cornea

Lesions in fluorescein stained corneas were clinically evaluated by biomicroscopy using a slit lamp (Haag Streit, Switzerland) with cobalt filter illumination. Photography of the fluorescein staining was taken with a slit lamp mounted camera (Topcon, Japan). At the end of each experiment, the rabbits were sacrificed and the cornea were excised, fixed in paraformaldehyde and examined for epithelial lesions.

D. Histological Examination

At the end of the treatment, the rabbits were sacrificed by a lethal dose of intravenously injected pentobarbitone. The eyes were enuclated and the corneas fixed in 4% paraformaldehyde. Corneas were embedded in paraffin blocks, sectioned, and with hematoxylin-eosine for light microscope examination.

II. Treatment of Corneal Epithelium Damage Caused by Conjunctival Epithelium Damage

Example 1

Rabbits with cornea damage induced as above were treated as follows: Five rabbits were treated with commercially available artificial tears (Lyteers™), five rabbits were treated with HDL (1 mg protein/ml) in phosphate buffered saline, five rabbits were treated with a commercially available lipid mixture (10% Intralipid™: 10% soybean oil, 1.2% egg phospholipids, 2.2% glycerol), and two rabbits were left untreated. Treatment consisted of applying two drops to the eye 3 times a day for seven consecutive days. The eyes were evaluated clinically during the experiment and pictures were taken every other day of the fluorescein stained corneas.

Figure 1:
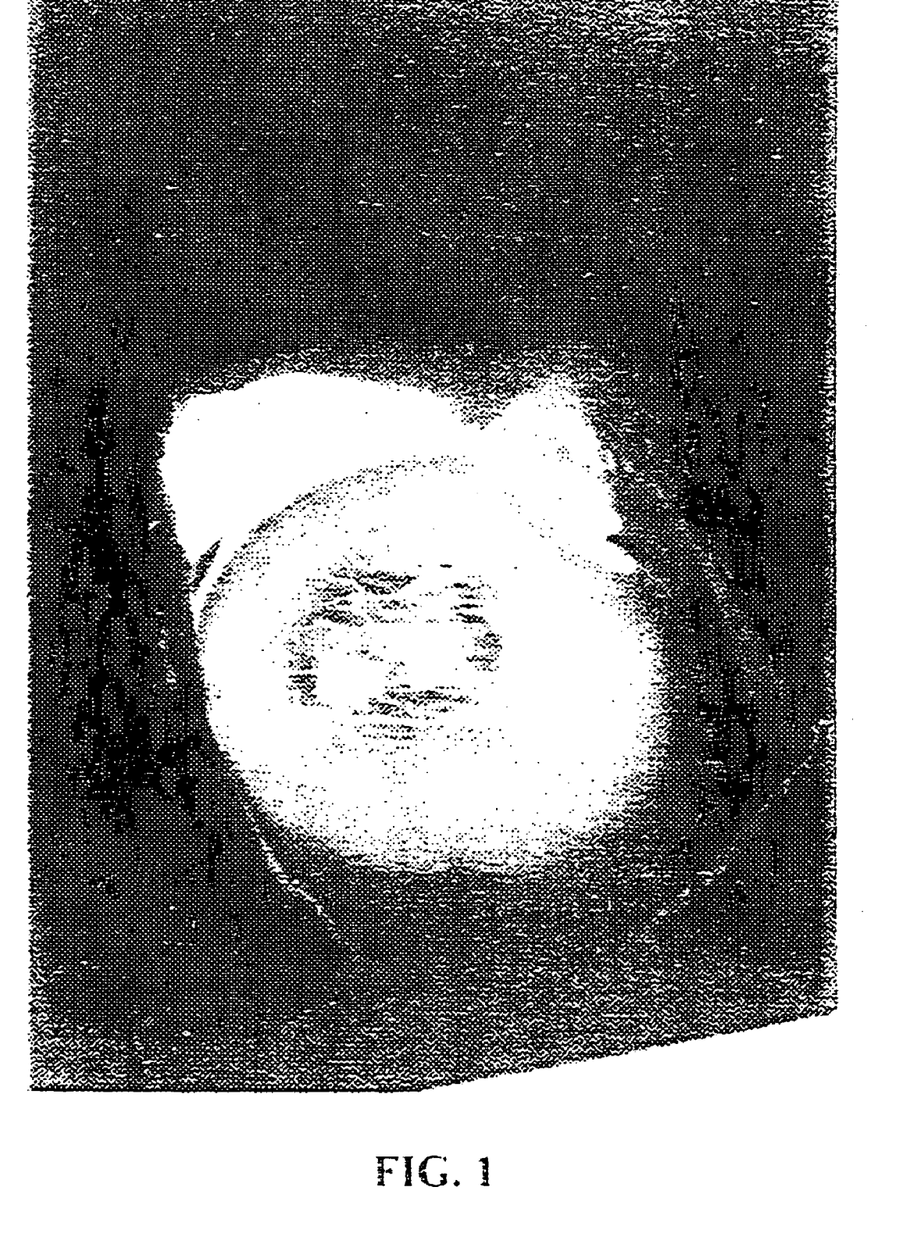
FIG. 1 shows fluorescein staining of untreated damaged eye cornea 5 days after surgery (×16)
Figure 2:
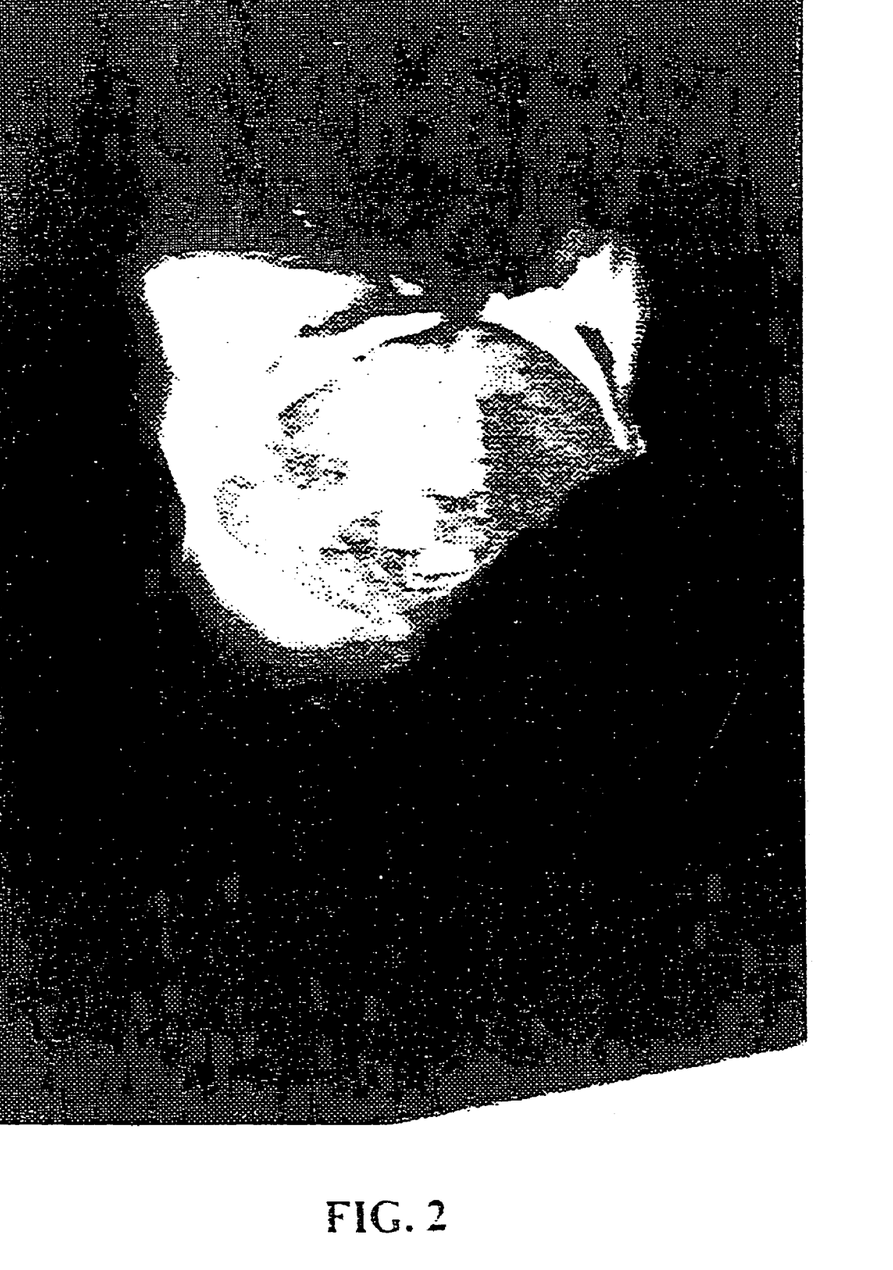
FIG. 2 shows fluorescein staining of untreated damaged eye cornea 12 days after surgery (×16)

Fluorescein staining of damaged eyes 5 and 12 days following surgery is shown in FIGS. 1 and 2, respectively. As can be seen, the surface of the untreated eye became progressively more scratched and opaque with time leading eventually to blurred vision.

Figure 3A:
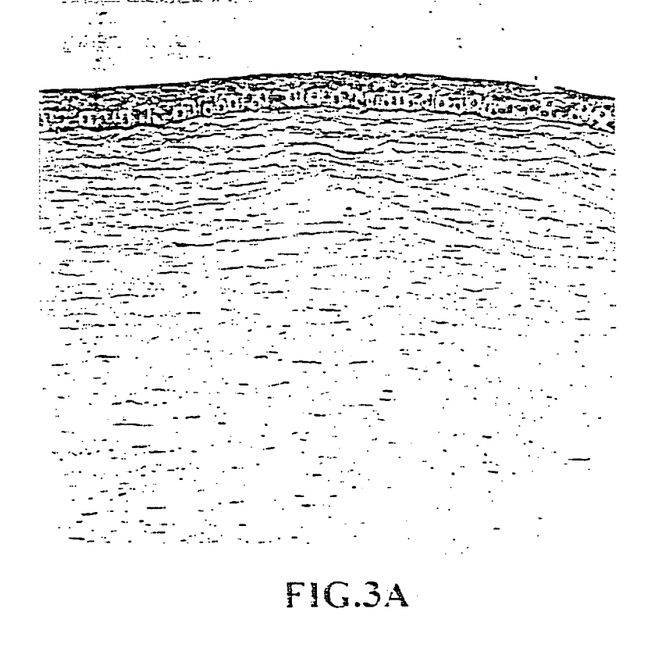
FIG. 3A shows the histological appearance of normal cornea.
Figure 3B:
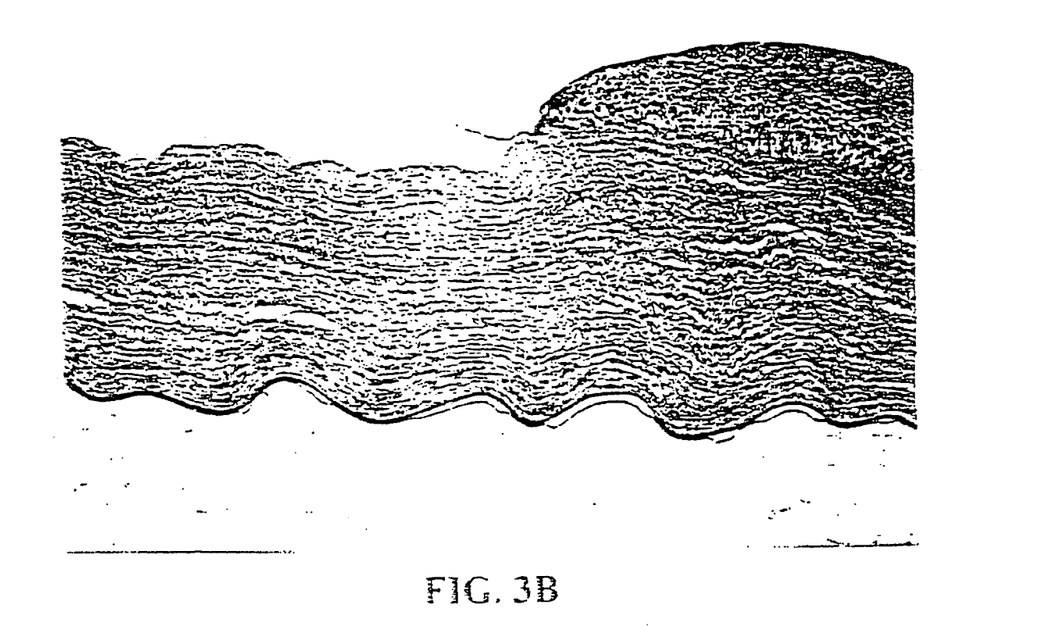
FIG. 3B shows the histological appearance of untreated damaged eye cornea 12 days after surgery.

Histological staining of damaged eye is shown in FIG. 3B and is compared to histological staining of normal eye 3A. As can be seen, in the damaged eye there has been complete erosion of the exposed epithelium due to persisant rubbing of the epithelium by the lids as well as severe keratitis and vascularization of the cornea.

Figure 4:
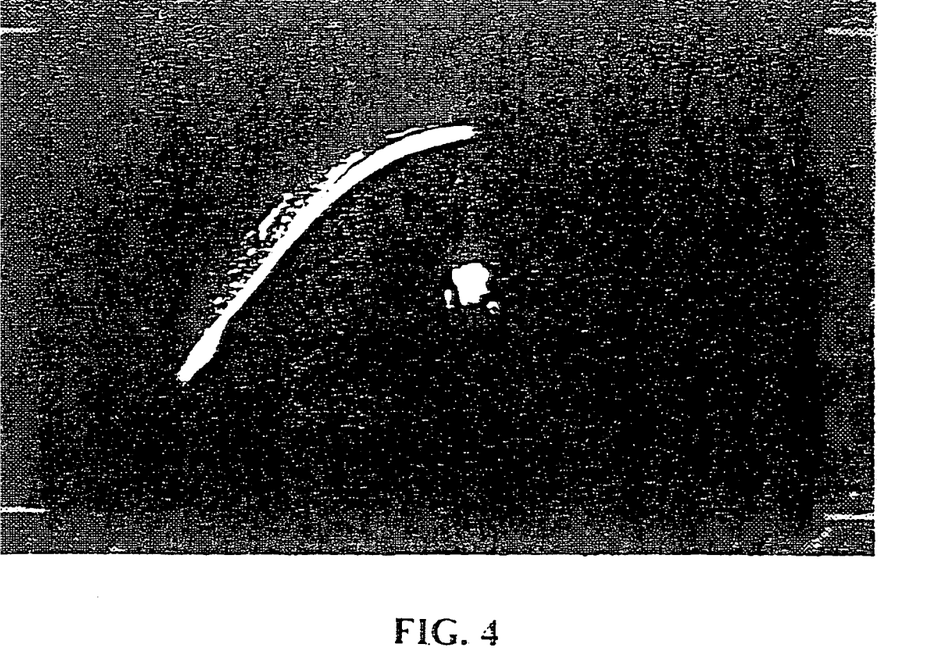
FIG. 4 shows fluorescein staining of damaged eye cornea following Intralipid™ treatment.
Figure 5:
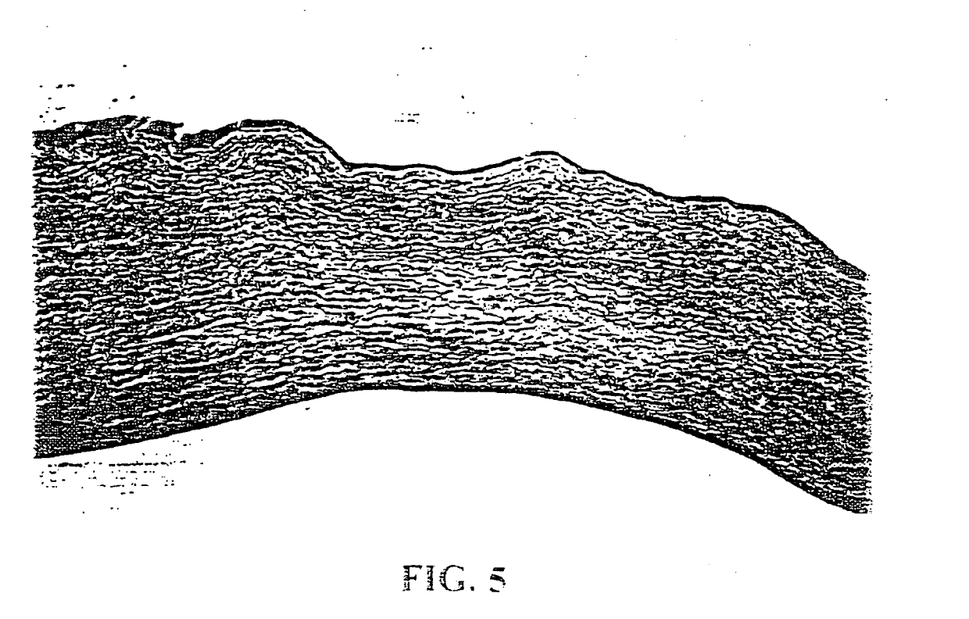
FIG. 5 shows the histological appearance of damaged eye cornea following Lyteers™ treatment.

Animal eyes that were treated with Intralipid™ show complete reversal to normal morphological structure as indicated by fluorescein staining (FIG. 4). However, animal eyes treated with Lyteers™, (FIG. 5) (commercially available artifical tears composed mainly of water and a viscous substance) did not return to normal. In contrast to normal eyes, the damaged area did not become covered again with normal layers of cuboidal epithelial cells and a single top layer of wing cells, but was covered instead by only a single layer of wing cells. These results indicate that artificial tears such as Lyeteers™ cannot promote regeneration of normal eye epithelium.

Figure 6:
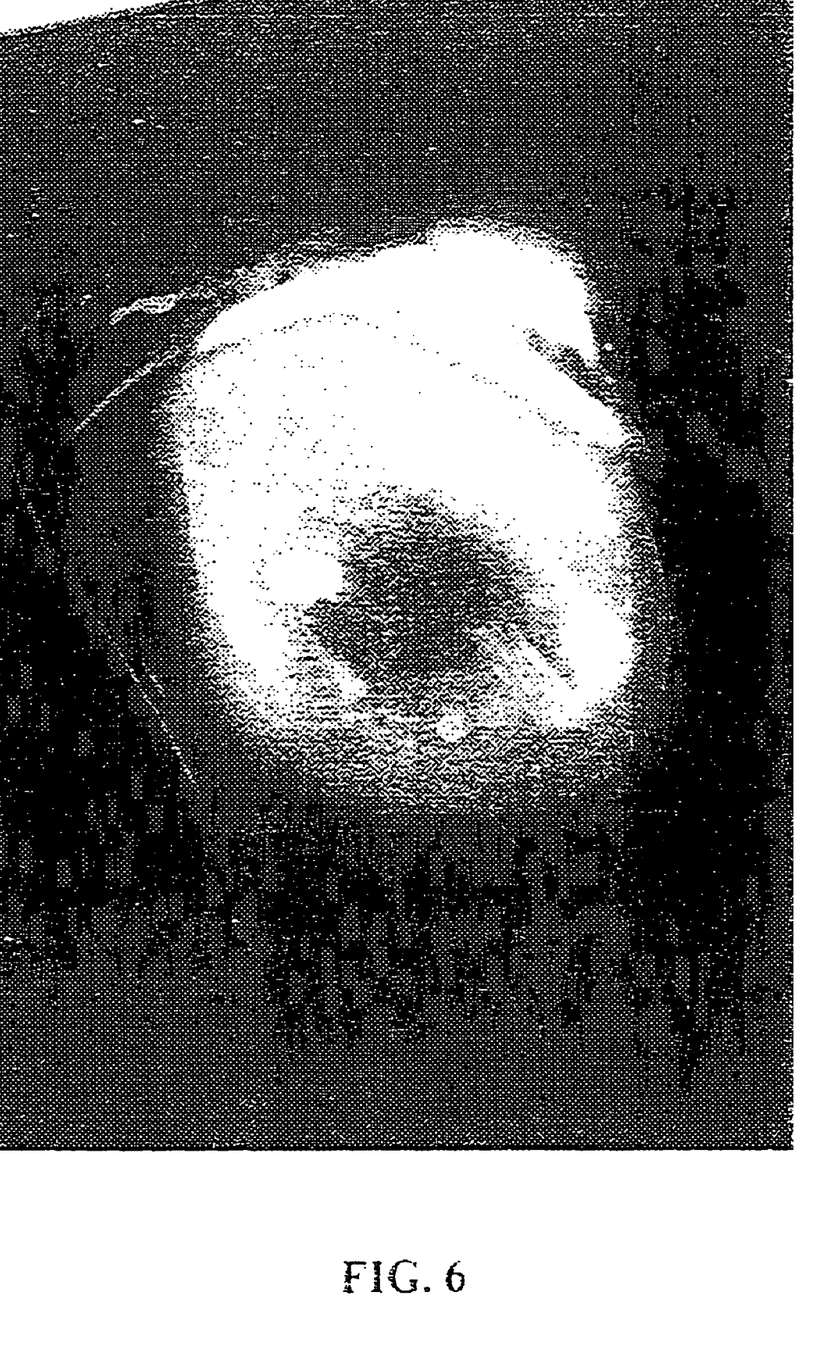
FIG. 6 shows fluorescein staining of damaged eye cornea after 3 days of treatment with HDL.
Figure 7:
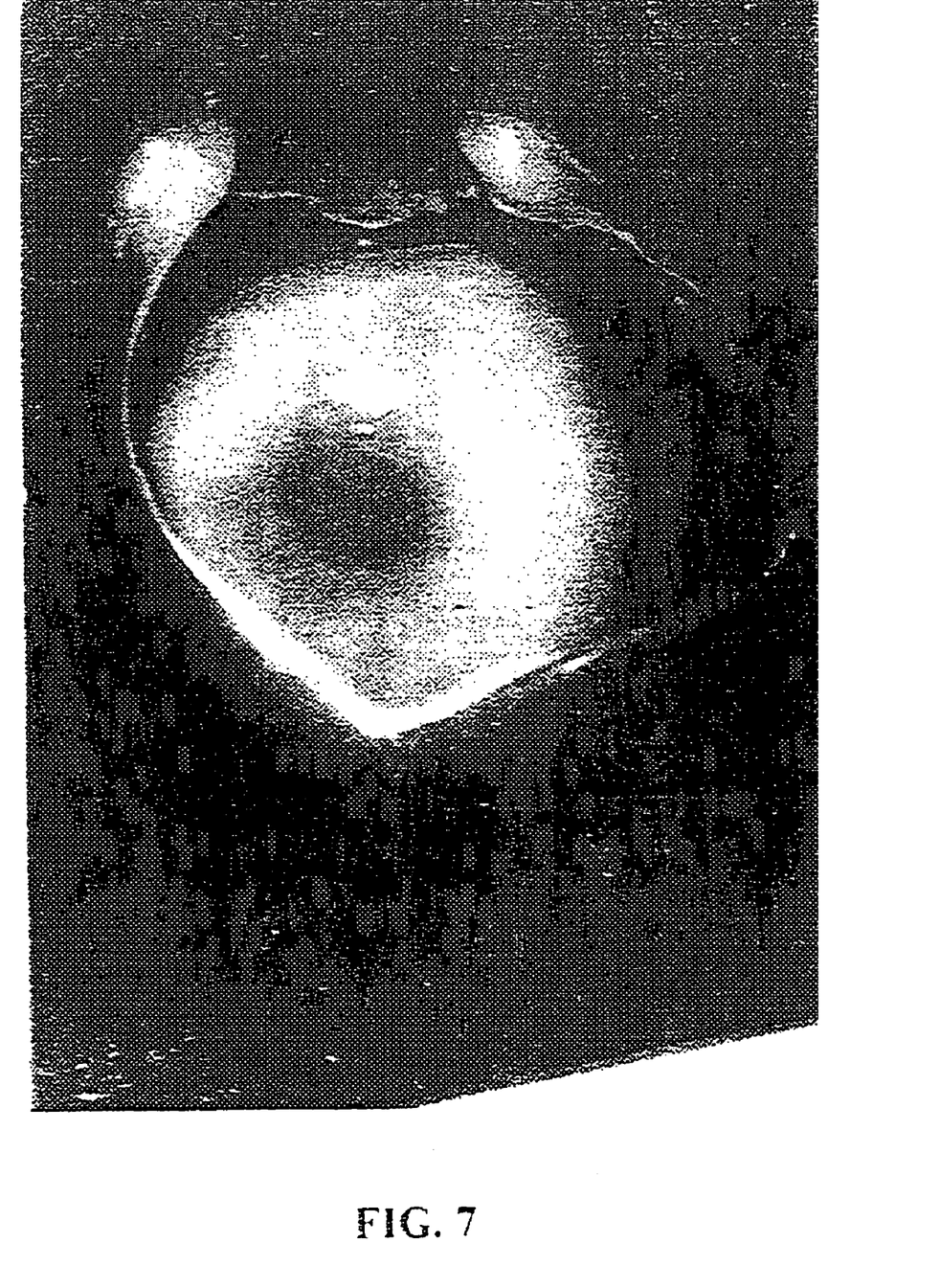
FIG. 7 shows fluorescein staining of damaged eye cornea at the end of treatment with HDL.
Figure 8:
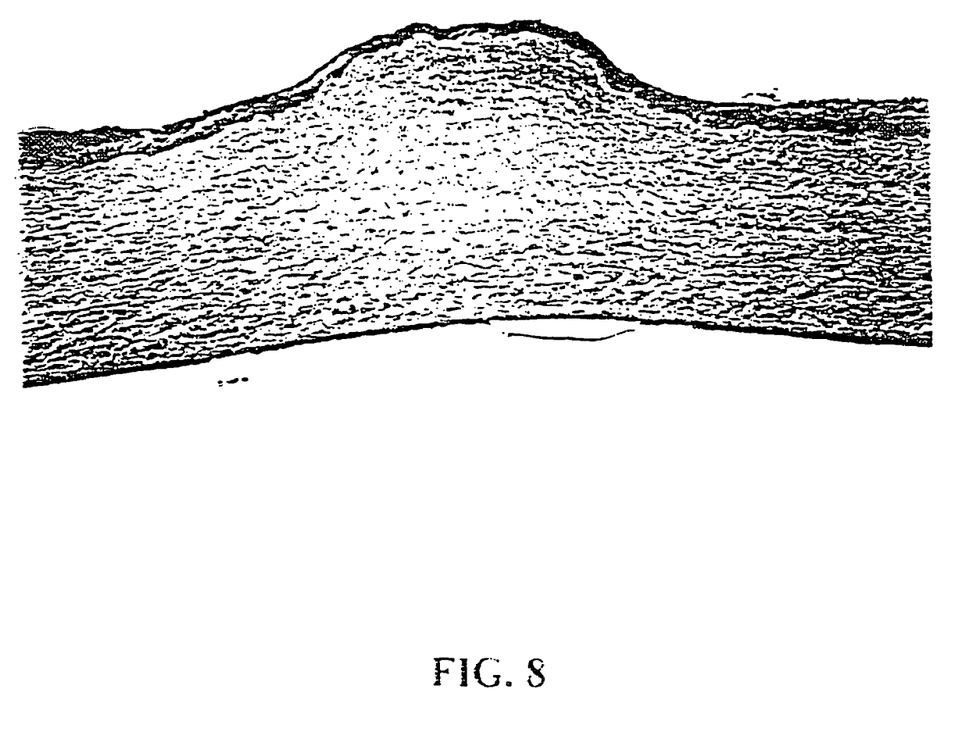
FIG. 8 shows the histological appearance of damaged eye cornea after HDL treatment.

In contrast to this, animal eyes treated with HDL showed essentially a complete return to normal morphological structure as indicated by fluorescein staining taken on the third day (FIG. 6) and at the end of treatment (FIG. 7) as well as by histological staining (FIG. 8). Histological staining shows essentially a complete return to normal of the eye epithelium characterized by formation of several layers of cuboidal cells and a single top layer of wing cells.

These results clearly indicate that both HDL and Intralipid™ are able to promote healing and regeneration of damaged eye epithelium and return to normal epithelium.

Example 2

Figure 9:
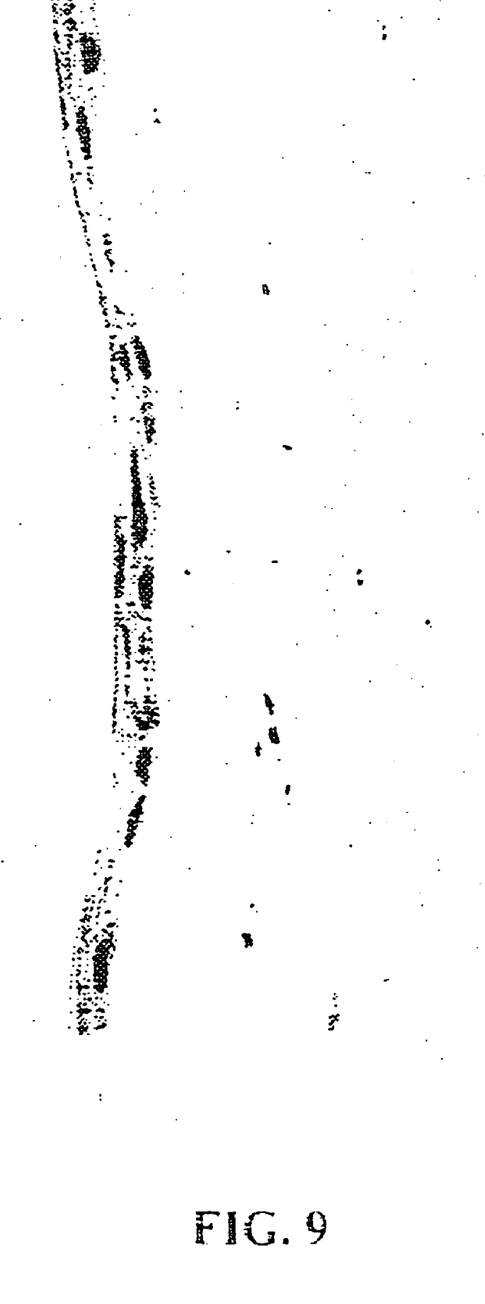
FIG. 9 shows the histological appearance of damaged eye cornea following 7 days of treatment with Lipofundin™.
Figure 10:
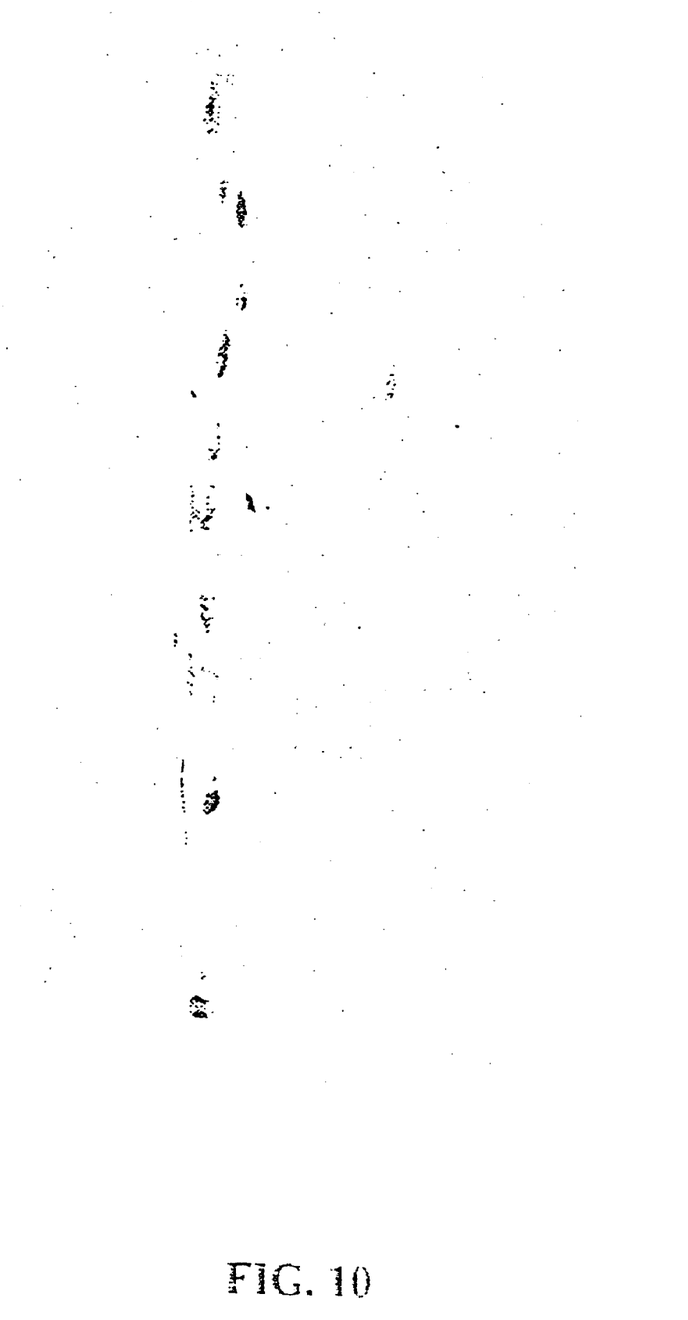
FIG. 10 shows the histological appearance of damaged eye cornea following 7 days of treatment with Lyeteers™.

Three rabbits underwent central corneal peeling of the epithelium in both eyes. The area of peeling, 8 mm in diameter, was first demarcated with trephine, and the epithelium excised with a scalpel. The right eye of each rabbit was treated with two drops of Lipofundin™ 10%, (a lipid mixture having: 5% soya oil, 5% medium chain triglycerides, 2.5% glycerol, and 1.2% egg lecithin) three times a day, while the left eye was treated with the same dose of Lyeteers™. The cornea were stained with fluorescein and photographed immediately after epithelium removal and on the third and fifth day afterwards. On the seventh day, the rabbits were sacrificed by a lethal dose of pental and the corneas were excised, fixed and stained for light microscopy. The denuded area in the fluorescein and fixed corneas was determined, and the extent of remaining damage calculated as the remaining denuded area divided by the initial denuded area. The results appear in Table 1 below which gives the fraction of initial damage remaining 0, 3, 5, and 7 days after peeling the epithelium. The results show that the rate of healing was faster in the Lipofundin™ treated eyes. FIGS. 9 and 10 show the epithelium of a Lipofundin™ treated eye and a treated eye, respectively, after 7 days of treatment.

TABLE 1

| Time | Treatment | |
|---|---|---|
| (Days) | Lipofundin ™ | Lyeteers ™ |
| 0 | 1.00 | 1.00 |
| 3 | .304 | .378 |
| 5 | .036 | .107 |
| 7 | 0 | 0 |

Although certain presently preferred embodiments of the present invention have been specifically described herein, it will be apparent to those skilled in the art to which the invention pertains that variations and modifications of the various embodiments shown and described herein may be made without departing from the spirit and scope of the invention. Accordingly, it is intended that the invention be limited only to the extent required by the appended claims and the applicable rules of law.

The invention claimed is:

1. A method of treating damaged eye epithelium or cornea or of the anterior segment of the eye, comprising:
administering or applying to a subject afflicted with a disorder or condition associated with eye epithelium, cornea or anterior segment damage, such damage comprising a corneal epithelial defect, corneal damage following radial keratectomy, membrane rupture, corneal damage associated with eye surgery, eye injury associated with aging, physical, chemical, radiation or medication damage, or chronic corneal edema, a therapeutic amount of an agent comprising one or more members selected from the group consisting of:
a high-density lipoprotein;
a reconstituted high-density lipoprotein; and
a combination of non-cholesterol lipid components capable of reconstituting a high-density lipoprotein comprising one or more of a sphingolipid and a phospholipid, and one or more of a glyceride and a triglyceride.

2. The method of claim 1, wherein the agent further comprises glycerol.

3. The method of claim 1, wherein the agent further comprises at least one apolipoprotein.

4. The method of claim 1, wherein the eye surgery associated with corneal damage comprises laser surgery, photorefractive keratectomy, or radial keratotomy.

5. The method of claim 1, wherein the corneal damage comprises epithelium or stroma damage.

6. The method of claim 1, wherein the radiation associated with eye injury comprises ultraviolet radiation or sunlight.

7. The method of claim 1, wherein the chronic corneal edema is associated with epithelium erosion or recurrent epithelium erosion.

8. The method of claim 1, wherein epithelial defect comprises a spontaneous peeling of the epithelium.

9. The method of claim 1, wherein the eye injury is associated with burns.

10. The method of claim 1, wherein the disorder or condition comprises spontaneous peeling or a systemic disorder or condition.

11. The method of claim 10, wherein the systemic disorder or condition comprises Sjogren syndrome, Steven-Johnson syndrome, Cicatricial pemphingoid syndrome, impaired tear film formation, or chronic edema of the cornea.

12. The method of claim 1, wherein the treating of damaged eye epithelium comprises symptom alleviation thereof.

13. The method of claim 1, wherein the eye epithelium comprises corneal and/or conjunctival epithelium.

14. The method of claim 13, wherein the corneal or conjunctival epithelium comprises epithelial cells or glands.

15. The method of claim 1, wherein the disorder or condition is associated with physical damage, chemical damage, a slow regeneration rate of epithelial cells, or diminished conjunctival glandular secretion.

16. The method of claim 1, wherein the disorder or condition comprises a disease or defect associated with systemic or topical medication.

17. The method of claim 1, wherein the agent further comprises albumin or an ophthalgesic agent.

18. The method of claim 17, wherein the ophthalgesic agent comprises one or more members selected from the group consisting of an epidermal growth factor, an attachment factor, an extracellular matrix component and a UV light protecting agent.

19. The method of claim 18, wherein
the epidermal growth factor comprises keratinocyte growth factor;
the attachment factor comprises laminin or fibronectin;
the extracellular matrix component comprises collagen or a heparin sulfate proteoglycan; and/or
the UV light protecting agent comprises oxybenzone.

20. The method of claim 1, wherein the agent is provided as a pharmaceutical composition further comprising an ophthalgesically acceptable carrier.

21. The method of claim 20, wherein the pharmaceutical composition comprises eye drops or a salve.

22. The method of claim 20, wherein the pharmaceutical composition comprises an emulsion, micelles or liposomes.

23. The method of claim 20, wherein the pharmaceutical composition comprises 0.1 to 20% agent.

24. The method of claim 20, wherein the pharmaceutical composition comprises 0.2 to 10% agent.

25. The method of claim 20, wherein the pharmaceutical composition comprises a hyperosmotic formulation.

26. The method of claim 1, wherein the agent causes a net efflux of cholesterol from cells.

27. The method of claim 1, wherein the disorder or condition comprises at least one of mechanical abrasion of the cornea, corneal epithelial defects created by contact lens wearing, corneal epithelial defects created by spontaneous peeling of the epithelium, corneal damage following photorefractive keratectomy, injuries caused by chemical substances, injuries caused by U.V. light exposure, corneal epithelium damage caused by medication, chronic edema of cornea with recurrent erosion of epithelium, and a condition caused by damage of epithelia due to radial keratotomy.

28. The method of claim 1, wherein the anterior segment of the eye comprises corneal epithelium and/or stromal conjunctiva.

29. The method of claim 15, wherein the slow rate of regeneration is associated with old age and/or the administration of antiproliferative substances.

30. The method of claim 1, wherein the high-density lipoprotein comprises at least one member selected from the group consisting of human high-density lipoprotein and bovine high-density lipoprotein.

31. The method of claim 1, wherein the phospholipid comprises at least one member selected from the group consisting of phosphatidyl choline, phosphatidylethanolamine, phosphatidylserine and phosphatidylinosital.

32. The method of claim 1, wherein the sphingolipid comprise at least one sphingomyelin.

33. The method of claim 3, wherein the apolipoprotein comprises at least one member selected from the group consisting of apolipoprotein A-I, apolipoprotein II, apolipoprotein E, apolipoprotein IV, and a combination of any two or more thereof.

34. The method of claim 1, wherein the agent comprises a lipid mixture having 5% soya oil, 5% medium chain triglycerides, 2.55 glycerol, and 1.2% egg lecithin or a lipid mixture having 10% soybean oil, 1.2% egg phospholipids, and 2.2% glycerol.

35. The method of claim 20, wherein the pharmaceutical composition further comprises one or more members selected from the group consisting of albumin, a growth factor, an attachment factor and an extracellular component.

36. The method of claim 35, wherein
the growth factor comprises at least one member selected from the group consisting of keratinocyte growth factor (KGF/FGF7), epidermal growth factor (EGF), and fibroblast growth factor (FGF);
the attachment factor comprises at least one member selected from the group consisting of laminin and fibronectin; and
the extracellular matrix component comprises at least one member selected from the group consisting of collagen and a heparan sulfate proteoglycan.

37. A method of treating damaged eye epithelium or cornea or of the anterior segment of the eye, comprising:
administering or applying to a subject afflicted with a disorder or condition associated with eye epithelium, cornea or anterior segment damage, such damage comprising a corneal epithelial defect, corneal damage following radial keratectomy, membrane rupture, corneal damage associated with eye surgery, eye injury associated with aging, physical, chemical, radiation or medication damage, or chronic corneal edema, a therapeutic amount of an agent comprising:
at least one member selected from the group consisting of a high-density lipoprotein and a non-cholesterol lipid component capable of reconstituting a high-density lipoprotein; and
at least one member selected from the group consisting of albumin and an ophthalgesic agent.

38. The method of claim 37, wherein the ophthalgesic agent comprises one or more members selected from the group consisting of an epidermal growth factor, an attachment factor, an extracellular matrix component, and a UV light protecting agent.

39. The method of claim 38, wherein
the epidermal growth factor comprises keratinocyte growth factor;
the attachment factor comprises laminin or fibronectin;
the extracellular matrix component comprises collagen or a heparin sulfate proteoglycan; and/or
the UV light protecting agent comprises oxybenzone.

40. A method of treating damaged eye epithelium or cornea or of the anterior segment of the eye, comprising:
administering or applying to a subject afflicted with a disorder or condition associated with eye epithelium, cornea or anterior segment damage, such damage comprising a corneal epithelial defect, corneal damage following radial keratectomy, membrane rupture, corneal damage associated with eye surgery, eye injury associated with aging, physical, chemical, radiation or medication damage, or chronic corneal edema, a therapeutic amount of a pharmaceutical composition comprising:
one or more members selected from the group consisting of a high-density lipoprotein and a non-cholesterol lipid component capable of reconstituting a high-density lipoprotein; and
an ophthalgesically acceptable carrier.

41. The method of claim 40, wherein the pharmaceutical composition comprises eye drops or a salve.

42. The method of claim 40, wherein the pharmaceutical composition comprises an emulsion, micelles or liposomes.

43. The method of claim 40, wherein the pharmaceutical composition comprises 0.1 to 20% agent.

44. The method of claim 40, wherein the pharmaceutical composition comprises 0.2 to 10% agent.

45. The method of claim 40, wherein the pharmaceutical composition comprises a hyperosmotic formulation.

46. A method of treating damaged eye epithelium or cornea, comprising corneal damage following radial keratectomy, or of the anterior segment of the eye, comprising:
administering or applying to a subject afflicted with a disorder or condition associated with a slow regeneration rate of epithelial cells caused by at least one of old age or administration of anti-proliferative substances, a therapeutic amount of an agent comprising
one or more members selected from the group consisting of a high-density lipoprotein and a non-cholesterol lipid component capable of reconstituting a high-density lipoprotein.

47. A method of treating damaged eye epithelium or cornea or of the anterior segment of the eye, comprising:
administering or applying to a subject afflicted with a disorder or condition associated with eye epithelium, cornea or anterior segment damage, such damage comprising a corneal epithelial defect, corneal damage following radial keratectomy, membrane rupture, corneal damage associated with eye surgery, eye injury associated with aging, physical, chemical, radiation or medication damage, or chronic corneal edema, a therapeutic amount of an agent comprising:
a high-density lipoprotein comprising at least one member selected from the group consisting of human high-density lipoprotein; bovine high-density lipoprotein; and reconstituted high-density lipoprotein comprising at least one apolipoprotein and one or more of a phospholipid and a sphingolipid.

48. A method of treating damaged eye epithelium or cornea or of the anterior segment of the eye, comprising:
administering or applying to a subject afflicted with a disorder or condition associated with eye epithelium, cornea or anterior segment damage, such damage comprising a corneal epithelial defect, corneal damage following radial keratectomy, membrane rupture, corneal damage associated with eye surgery, eye injury associated with aging, physical, chemical, radiation or medication damage, or chronic corneal edema, a therapeutic amount of an agent comprising a lipid mixture having 5% soya oil, 5% medium chain triglycerides, 2.55 glycerol, and 1.2% egg lecithin or a lipid mixture having 10% soybean oil, 1.2% egg phospholipids, and 2.2% glycerol.

49. The method of claim 40, wherein the pharmaceutical composition further comprises one or more members selected from the group consisting of albumin, a growth factor, an attachment factor, and an extracellular component.

50. The method of claim 49, wherein
the growth factor comprises at least one member selected from the group consisting of a keratinocyte growth factor, an epidermal growth factor and a fibroblast growth factor;
the attachment factor comprises at least one member selected from the group consisting of laminin and fibronectin; and/or
the extracellular matrix component comprises at least one member selected from the group consisting of collagen and a heparan sulfate proteoglycan.

51. A method for treating disorders of the anterior segment of the eye comprising corneal damage following radial keratectomy, comprising administering to a subject in need of such treatment a therapeutically effective amount of a composition comprising one or more high-density lipoproteins selected from the group consisting of:
a natural high-density lipoprotein; and
a reconstituted high-density lipoprotein.

52. The method of claim 51, wherein the reconstituted high-density lipoprotein comprises a combination of at least one apolipoprotein and at least one non-cholesterol containing lipid component capable of reconstituting a high-density lipoprotein.

53. The method of claim 52, wherein the at least one non-cholesterol containing lipid component capable of reconstituting a high-density lipoprotein comprises one or more members selected from the group consisting of a phospholipid, a spingolipid, a glyceride, a triglyceride, and glycerol.

54. The method of claim 51, wherein the natural high-density lipoprotein comprises one or more members selected from the group consisting of human high-density lipoprotein and bovine high-density lipoprotein.

55. A method for treating disorders of the anterior segment of the eye comprising corneal damage following radial keratectomy, comprising administering to a subject in need of such treatment a therapeutically effective amount of a composition comprising a combination of non-cholesterol lipid components capable of reconstituting a high-density lipoprotein comprising one or more of a sphingolipid and a phospholipid, and one or more of a glyceride and a triglyceride.

56. A method for treating disorders, comprising corneal damage following radial keratectomy, of the anterior segment of the eye comprising administering to a subject in need of such treatment a therapeutically effective amount of a composition comprising a lipid mixture having 5% soya oil, 5% medium chain triglycerides, 2.55 glycerol, and 1.2% egg lecithin.

57. A method for treating disorders, comprising corneal damage following radial keratectomy, of the anterior segment of the eye comprising administering to a subject in need of such treatment a therapeutically effective amount of a composition comprising a lipid mixture having 10% soybean oil, 1.2% egg phospholipids, and 2.2% glycerol.

58. The method of claim 1, wherein the agent is a high-density lipoprotein.

59. The method of claim 1, wherein the agent is a reconstituted high-density lipoprotein.

60. The method of claim 1, wherein the agent is a combination of non-cholesterol lipid components capable of reconstituting a high-density lipoprotein comprising one or more of a sphingolipid and a phospholipid, and one or more of a glyceride and a triglyceride.

61. The method of claim 1, wherein the agent is reconstituted high-density lipoprotein and a combination of non-cholesterol lipid components capable of reconstituting a high-density lipoprotein comprising one or more of a sphingolipid and a phospholipid, and one or more of a glyceride and a triglyceride.

* * * * *

UNITED STATES PATENT AND TRADEMARK OFFICE
CERTIFICATE OF CORRECTION

| | | |
|---|---|---|
| PATENT NO. | : 7,723,287 B1 | Page 1 of 1 |
| APPLICATION NO. | : 09/341048 | |
| DATED | : May 25, 2010 | |
| INVENTOR(S) | : Naphtali Savion et al. | |

It is certified that error appears in the above-identified patent and that said Letters Patent is hereby corrected as shown below:

Column 6, Line 10
Please delete "and with hematoxylin-eosine" and replace with -- and stained with hematoxylin-eosine --

Column 7, Line 19
Please delete "and a treated eye" and replace with -- and a Lyeteers™ treated eye --

Column 9, Claim 31, Line 17
Please delete "and phosphatidylinosital" and replace with -- and phosphatidylinositol --

Column 9, Claim 33, Lines 22-23
Please delete "apolipoprotein A-I, apolipoprotein II, apolipoprotein E, apolipoprotein IV"
and replace with -- apolipoprotein A-I, apolipoprotein A-II, apolipoprotein E, apolipoprotein A-IV --

Column 9, Claim 34, Line 27
Please delete "2.55 glycerol" and replace with -- 2.5% glycerol --

Column 11, Claim 48, Line 9
Please delete "2.55 glycerol" and replace with -- 2.5% glycerol --

Column 12, Claim 56, Line 21
Please delete "2.55 glycerol" and replace with -- 2.5% glycerol --

Signed and Sealed this

Thirtieth Day of November, 2010

David J. Kappos
*Director of the United States Patent and Trademark Office*